(12) United States Patent
Iyunni

(10) Patent No.: US 11,628,074 B2
(45) Date of Patent: Apr. 18, 2023

(54) TELESCOPING STENTS

(71) Applicant: SAINATH INTELLECTUAL PROPERTIES, LLC, Pinellas Park, FL (US)

(72) Inventor: Venkata Sesha Sayi Nath Iyunni, Pinellas Park, FL (US)

(73) Assignee: SAINATH INTELLECTUAL PROPERTIES, LLC, Pinellas Park, FL (US)

( * ) Notice: Subject to any disclaimer, the term of this patent is extended or adjusted under 35 U.S.C. 154(b) by 0 days.

(21) Appl. No.: 17/435,013

(22) PCT Filed: Jan. 19, 2021

(86) PCT No.: PCT/US2021/013920
§ 371 (c)(1),
(2) Date: Aug. 30, 2021

(87) PCT Pub. No.: WO2022/159075
PCT Pub. Date: Jul. 28, 2022

(65) Prior Publication Data
US 2022/0226132 A1 Jul. 21, 2022

(51) Int. Cl.
*A61F 2/852* (2013.01)
*A61F 2/848* (2013.01)

(52) U.S. Cl.
CPC .............. *A61F 2/852* (2013.01); *A61F 2/848* (2013.01); *A61F 2220/0075* (2013.01)

(58) Field of Classification Search
CPC ... A61F 2/852; A61F 2220/0075; A61F 2/848
See application file for complete search history.

(56) References Cited

U.S. PATENT DOCUMENTS

| | | | |
|---|---|---|---|
| 6,176,881 B1* | 1/2001 | Schar | A61F 2/44 623/17.13 |
| 6,325,823 B1 | 12/2001 | HORZEWSKI et al. | |
| 6,852,123 B2* | 2/2005 | Brown | A61F 2/91 623/1.15 |
| 8,343,204 B2 | 1/2013 | Osborne | |
| 9,937,067 B2 | 4/2018 | Pendleton et al. | |
| 2001/0049554 A1* | 12/2001 | Ruiz | A61F 2/07 623/1.35 |
| 2002/0107560 A1* | 8/2002 | Richter | A61F 2/91 623/1.11 |
| 2002/0151957 A1* | 10/2002 | Kerr | A61F 2/07 623/1.13 |

(Continued)

OTHER PUBLICATIONS

Written Opinion of Intl. PCT Application No. PCT/US2021/013920 dated Mar. 29, 2021.
Extended European Search Report—dated Feb. 25, 2022.

*Primary Examiner* — Jing Rui Ou
(74) *Attorney, Agent, or Firm* — Carlton Fields, PA; Eleanor Yost

(57) ABSTRACT

The invention described herein relates to telescoping stents. The embodiments described herein allow for adequate securement to, accommodation for movement by, and prevention of injury of tubular organs or hollow areas of the body. Certain embodiments relate to telescoping steins with loop interlocking mechanisms. Further embodiments relate to telescoping stents with ball-in-groove interlocking mechanisms.

21 Claims, 5 Drawing Sheets

(56) References Cited

U.S. PATENT DOCUMENTS

| | | |
|---|---|---|
| 2005/0113905 A1 | 5/2005 | Greenberg et al. |
| 2007/0055350 A1* | 3/2007 | Erickson .................. A61F 2/07 623/1.16 |
| 2009/0138083 A1* | 5/2009 | Biyani ..................... A61F 2/44 623/17.11 |
| 2011/0093002 A1* | 4/2011 | Rucker .................... A61F 2/90 606/198 |
| 2013/0197657 A1* | 8/2013 | Anca ....................... A61F 2/07 623/23.7 |
| 2020/0281711 A1 | 9/2020 | McDermott et al. |

\* cited by examiner

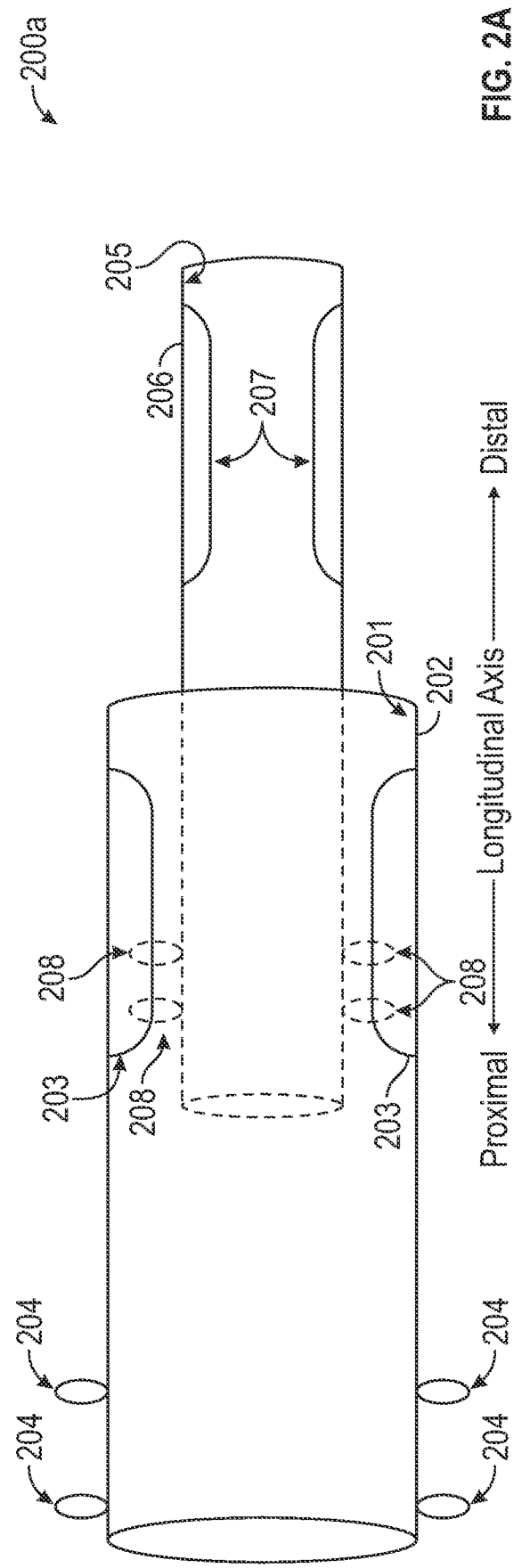
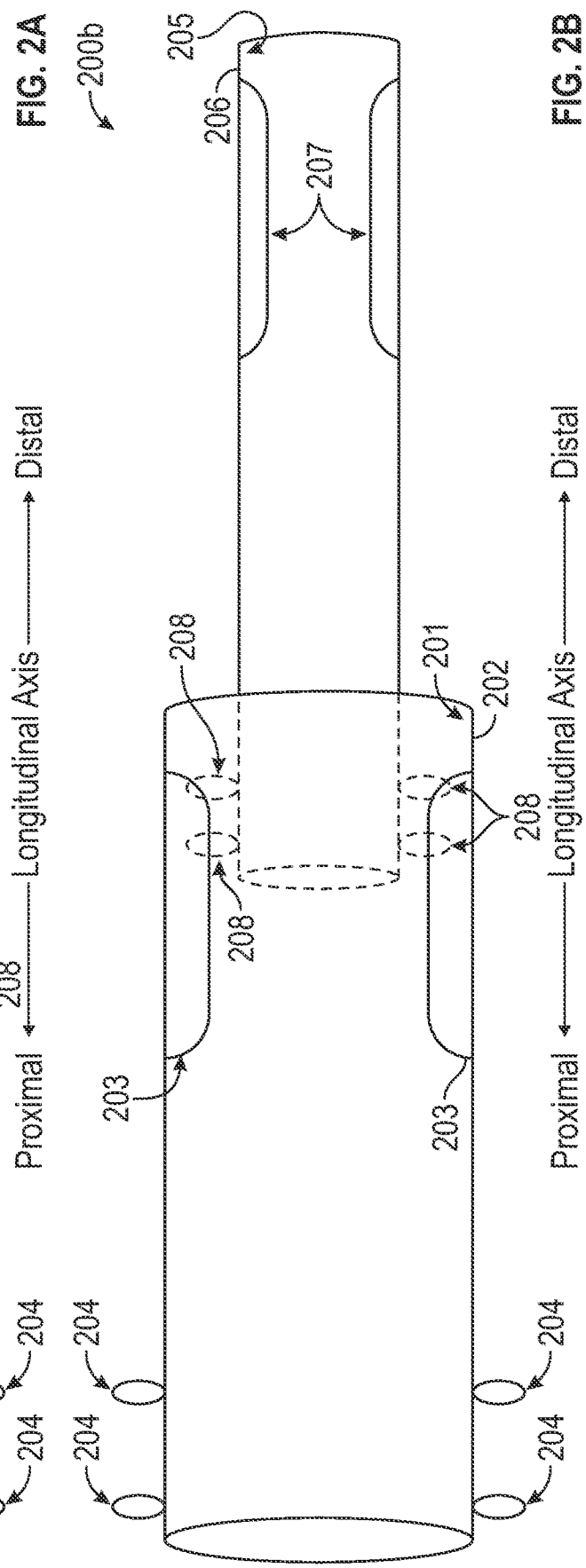

TELESCOPING STENTS

CROSS-REFERENCE TO RELATED APPLICATIONS

This application is a national stage application, filed under 35 U.S.C. § 371, of International Patent Application No. PCT/US2021/013920, filed on Jan. 19, 2021, which is incorporated by reference herein in its entirety.

FIELD OF THE INVENTION

This present invention relates to telescoping stents.

BACKGROUND

Some medical treatments or procedures require deploying a flexible tubular structure within a tubular organ or hollow area of the body, and leaving that tubular structure within that organ or area of the body for an extended period of time. For example, a stent may be placed in a tubular organ within a patient's digestive tract, such as a region of stomach or intestine. This could allow food or other matter consumed by the patient to pass from the patient's mouth, into the digestive tract, through the stoat, and eventually to a distal region of the digestive tract. While this food or other consumed matter is passing through the stent, it is not coming in contact with the surrounding gut wall in that portion of the digestive tract. Those of skill in the art will recognize that this effect may be desired for various existing or potential medical treatments or procedures, such as weight loss or nutritional Unbalance (modulating, controlling, or limiting nutrient absorption), inflammatory bowel disease (minimizing irritation to portions of inflamed tissue), or post-operative recovery (protecting tissue that was recently operated on, or tissue that was transplanted thus newly introduced, horn potentially damaging physical contact, therefore allowing said tissue to grow and heal).

Current stems have at least two significant drawbacks. First, current stents do not adequately secure to tubular organs or hollow areas of the body. This prevents the stent from being deployed in the desired location for an extended period of time. Further, current attachment mechanisms for stents apply too much pressure and/or strain to and/or on the attachment points. Such mechanisms include pyloric or jejunal anchoring. Current attachment mechanisms can harm the native tissue and prevent the stent from being deployed for an extended period of time. Possible injuries may include rupture, tear, trauma, complication, incarceration, strangulation, ischemia, infarct, iatrogenic injury, a combination thereof, etc. There is need for a stein with a secure attachment mechanism that ensures the stent will mot be displaced.

A second drawback with current stents is limited flexibility. Current stents to not adequately accommodate for expected movement of tubular organs or hollow areas of the body, such as peristalsis, muscular contraction, movements induced by positional, gravitational, kinetic, or other forces, a combination thereof, etc. Current stents, for example, while adequately secured within the body may not adequately permit dynamic peristalsis within the entire gastrointestinal system. There is therefore need for a stent that allows the device to extend or contract without dislodging.

U.S. Pat. No. 8,012,140, for example, discloses a gastrointestinal sleeve device having an elongate tubular body, with a proximal opening and a distal opening, which can be attached near its proximal opening at the native gastroesophageal junction. The stent disclosed does not allow for adequate securement to, accommodation for movement by, and prevention of injury of tubular organs or hollow areas of the body. The stent disclosed does not disclose dual securement, non-traumatic securement, nor multiple floating/telescoping segments.

While the embodiments described herein focus primarily on applications in human medicine, those skilled in the at will recognize that the embodiments described herein have applications in any setting where a flexible tubular structure capable of secure attachment and long-term deployment is desired.

SUMMARY OF THE INVENTION

Embodiments described herein allow for adequate securement to, accommodation for, movement by, and prevention of injury of tubular organs or hollow areas of the body.

Certain embodiments relate to variably telescoping stents with loop interlocking mechanisms.

Certain embodiments also relate to variably telescoping stents with ball-in-groove interlocking, mechanisms.

BRIEF DESCRIPTION OF THE DRAWINGS

Other features of the embodiments described herein will become apparent from the attached drawings, which illustrate embodiments of certain telescoping, stents and their component parts, wherein:

FIG. 2A illustrates loop interlocking mechanisms of tubular segments of a telescoping stent.

FIG. 2B illustrates loop interlocking mechanisms of tubular segments of a telescoping stent.

DETAILED DESCRIPTION

While the following describes embodiments of devices according to the present invention, it is understood that this description is to be considered only illustrative of the principles of the inventions described herein and is not to be limitative thereof. Numerous other variations, all within the scope of the claims, will readily occur to those of ordinary skill in the art.

The definitions and meanings of terms used herein shall be apparent from the description, the figures, and the context in which the terms are used.

Certain preferred embodiments can be used in one or more tubular organs or hollow areas of the body, including, but not limited to the human mouth, oral cavity, nasal cavity, pharynx, larynx, trachea, bronchi, esophagus, stomach, intestines, colon, rectum, gynecological organs, bladder, biliary ducts, pancreatic duct, or urethra, etc., or a combination thereof.

In certain preferred embodiments, the telescoping stent comprises a proximal anchoring member, distal anchoring member, and two or more tubular segments with loop interlocking mechanisms.

Figure 1A:
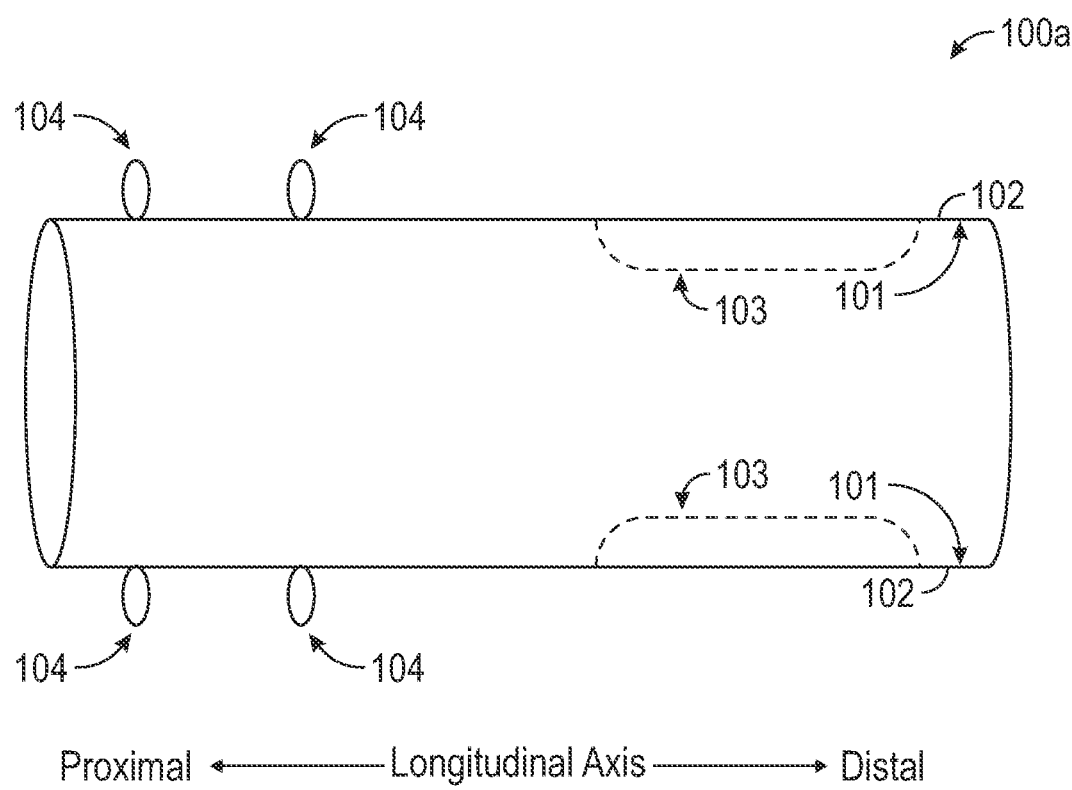
FIG. 1A illustrates a tubular segment of a telescoping stent with loop interlocking mechanisms.
Figure 1B:
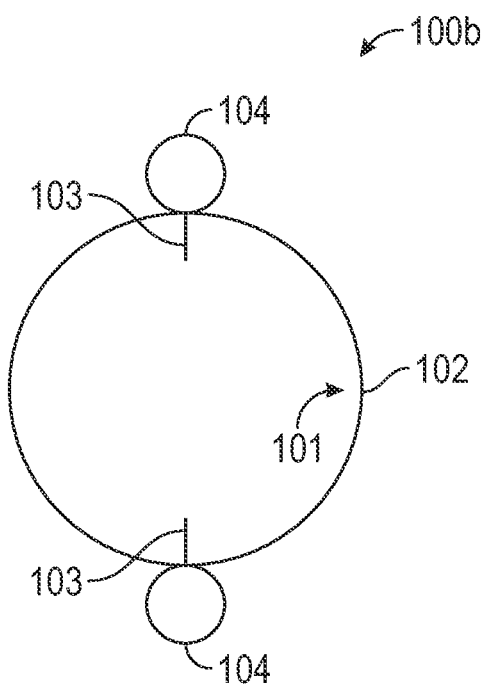
FIG. 1B illustrates a tubular segment of a telescoping stent with loop interlocking mechanisms.

FIGS. 1A and 1B illustrate embodiments of tubular segments 100a and 100b that can be used in a telescoping stent with loop interlocking mechanisms. Tubular segments 100a and 100b comprise an interior wall 101 and an exterior wall 102. Interior wall 101 further comprises one or more longitudinal loops 103. Exterior wall 102 further comprises one or more perpendicular loops 104. Tubular segment 100a is illustrated in a side view along its longitudinal axis. Tubular segment 100b is illustrated along its cross-sectional plane at a point in the longitudinal axis including perpendicular loops 104.

Each longitudinal loop 103 further comprises a proximal end and a distal end. The cross-sectional plane of each longitudinal loop 103 is roughly parallel to the longitudinal axis of tubular segment 100a and extends radially inward from the cross-sectional plane of tubular segment 100b. Each perpendicular loop 104 further comprises a cross-sectional plane. The cross-sectional plane of each perpendicular loop 104 is roughly parallel to the cross-sectional plane of tubular segment 100b and extends radially outward from the cross-sectional plane of tubular segment 100b.

FIGS. 2A and 2B illustrate the loop interlocking mechanisms of tubular segments like the tubular segment illustrated in FIGS. 1A and 1B, where the tubular segments have different diameters and each tubular segment overlaps in part along the longitudinal axis with the other tubular segments until reaching the final or innermost (smallest diameter) tubular segment, which does not overlap another tubular segment. The loop interlocking mechanism shown in FIGS. 2A and 2B is not limited to two tubular segments and can be used in embodiments of the invention that include three or more tubular segments, wherein larger diameter tubular segments overlap and interlock with smaller diameter tubular segments until reaching the final or innermost (smallest diameter) tubular segment, which does not overlap another tubular segment.

In this embodiment, the outer tubular segment has a larger diameter compared to the diameter of an inner tubular segment, and comprises an interior wall 201 and an exterior wall 202. Interior wall 201 further comprises one or more longitudinal loops 203 and exterior wall 202 further comprises one or more perpendicular loops 204. The inner tubular segment comprises an interior wall 205 and an exterior wall 206 wherein interior wall 205 further comprises one or more longitudinal loops 207, and exterior wall 206 further comprises one or more perpendicular loops 208. Each longitudinal loop 203 of the larger diameter tubular segment interlocks with one or more perpendicular loops 208 of the smaller diameter tubular segment.

Overlapping tubular segments are at maximum overlap 200a when the proximal end of a longitudinal loop 203 makes contact with the most proximal perpendicular loop 208 through which it interlocks. Overlapping tubular segments are at minimum overlap 200b when the distal end of a longitudinal loop 203 makes contact with the most distal perpendicular loop 208 through which it interlocks. In certain embodiments, the maximum overlap of tubular segments is 50% or less of the length of the smaller diameter tubular segment.

The loop interlocking mechanisms described herein allow for telescoping steels that adequately accommodate for expected movement of tubular organs or hollow areas of the body where the stent is deployed. The segments of the sleet extend or contract independently and the multiple telescoping segments can float freely within a desired range of motion. The extension of the telescoping segments is limited by minimum and overlap as described above, where the interlocking loops reach a maximum extension.

Different embodiments can have different levels of desired flexibility versus rigidity. For more rigidity, more longitudinal loops, more perpendicular loops, or more perpendicular loops per longitudinal loop can be used. For more flexibility, less longitudinal loops, less perpendicular loops, or less perpendicular loops per longitudinal loop can be used. Different levels of desired flexibility versus rigidity can also be achieved by modulating the materials that comprise the components of these embodiments.

In certain embodiments, tubular segments comprise medical grade silicone, latex, polyurethane, stainless steel, or medical grade plastic, in certain embodiments, longitudinal loops comprise medical grade silicone, latex, polyurethane, plastic, Dacron, or silk. In certain embodiments, perpendicular loops comprise medical grade silicone, latex, polyurethane, plastic, Dacron, or silk.

In certain embodiments, tubular segments are about 1.0-5.0 cm in length with an approximate diameter of 5.0-30.0 mm (15 Fr to 90 Fr). In certain embodiments, longitudinal loops are ovoid or rectangular in shape. In certain embodiments, longitudinal loops are about 0.1-4.0 cm in length and about 1.0-5.0 mm in width. In certain embodiments, perpendicular loops have a diameter of about 1.0-5.0 mm. In certain embodiments, perpendicular loops are triangular, quadrangular, or orthogonal in shape. In some embodiments the loops may be made of elastic material.

In certain embodiments, interior walls do not comprise longitudinal loops but further comprise perpendicular loops. In certain embodiments, exterior walls do not comprise perpendicular loops but further comprise longitudinal loops.

In certain embodiments, the innermost tubular segment of an assembly, the outermost tubular segment of an assembly, or both, can be modified such that the external surface of the assembly, the internal surface of the assembly, or both, are smooth. In certain preferred embodiments, the innermost tubular segment of a telescoping stent may comprise an interior wall that does not comprise longitudinal or perpendicular loops, in certain preferred embodiments, the outermost tubular segment of a telescoping stent may comprise an exterior wall that does not comprise longitudinal or perpendicular loops.

In certain certain embodiments, the telescoping stent further comprises a one-way sock valve fixed to the distal end of the innermost tubular segment of the telescoping stent. The one-way sock valve may be interconnected to the innermost tubular segment via perpendicular loops on the external surface of the valve that interconnect with longitudinal loops on the internal surface of the innermost tubular segment. The one-way sock valve may also be interconnected to the innermost tubular segment via longitudinal loops on the external surface of the valve that interconnect with perpendicular loops on the internal surface of the innermost tubular segment. The one-way sock valve can also be fixed to the distal end of a telescoping stent through any other means known in the art. One non-limiting example of a one-way sock valve that can be used with the invention is described in U.S. Pat. No. 10,758,382.

In another embodiment, the telescoping stent comprises a proximal anchoring member, distal anchoring member, and two or more tubular segments with groove interlocking mechanisms.

Figure 3A:
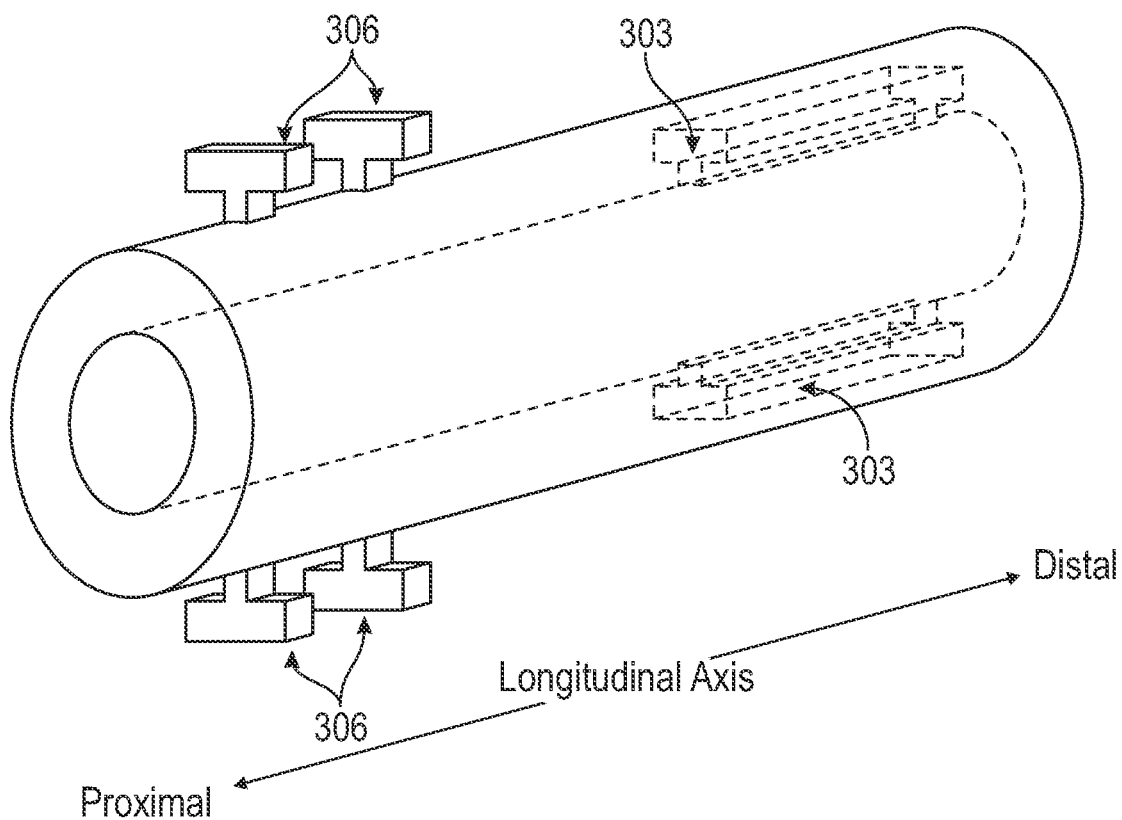
FIG. 3A illustrates a tubular segment of a telescoping stent with ball-in-groove interlocking mechanisms.
Figure 3B:
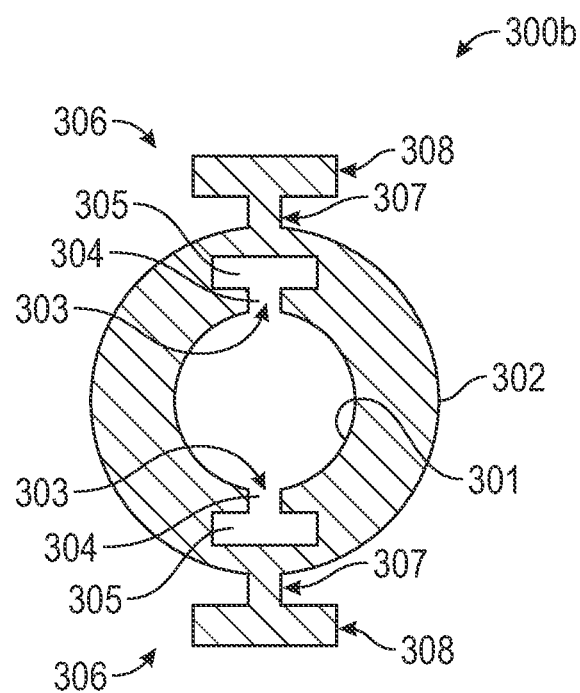
FIG. 3B illustrates a tubular segment of a telescoping stent with ball-in-groove interlocking mechanisms.

FIGS. 3A and 3B illustrate an embodiment of a tubular segment 300a and 300b that can be used in a telescoping stent with ball-in-groove interlocking mechanisms. Tubular segments 300a and 300b comprise an interior wall 301 and an exterior wall 302. interior wall 301 further comprise one or more receivers 303. Exterior wall 302 further comprises one or more insertors 306. Each receiver 303 further comprises a proximal end, a distal end, a vestibule 304, and a track 305 along the longitudinal axis. Vestibule 304 is than, located interior to, and continuous with track 305. Each insertor 306 further comprises a neck 307 and a head 308. Neck 307 is narrower than, interior to, and continuous with head 308. Tubular segment 300a is illustrated in a side cutaway view along its longitudinal axis. Receivers 303, including their respective vestibules 304 and tracks 305, extend along the longitudinal axis of tubular segment 300a. Tubular segment 300b is illustrated in a cutaway view looking down the longitudinal axis front the proximal end to the distal end.

Figure 3C:
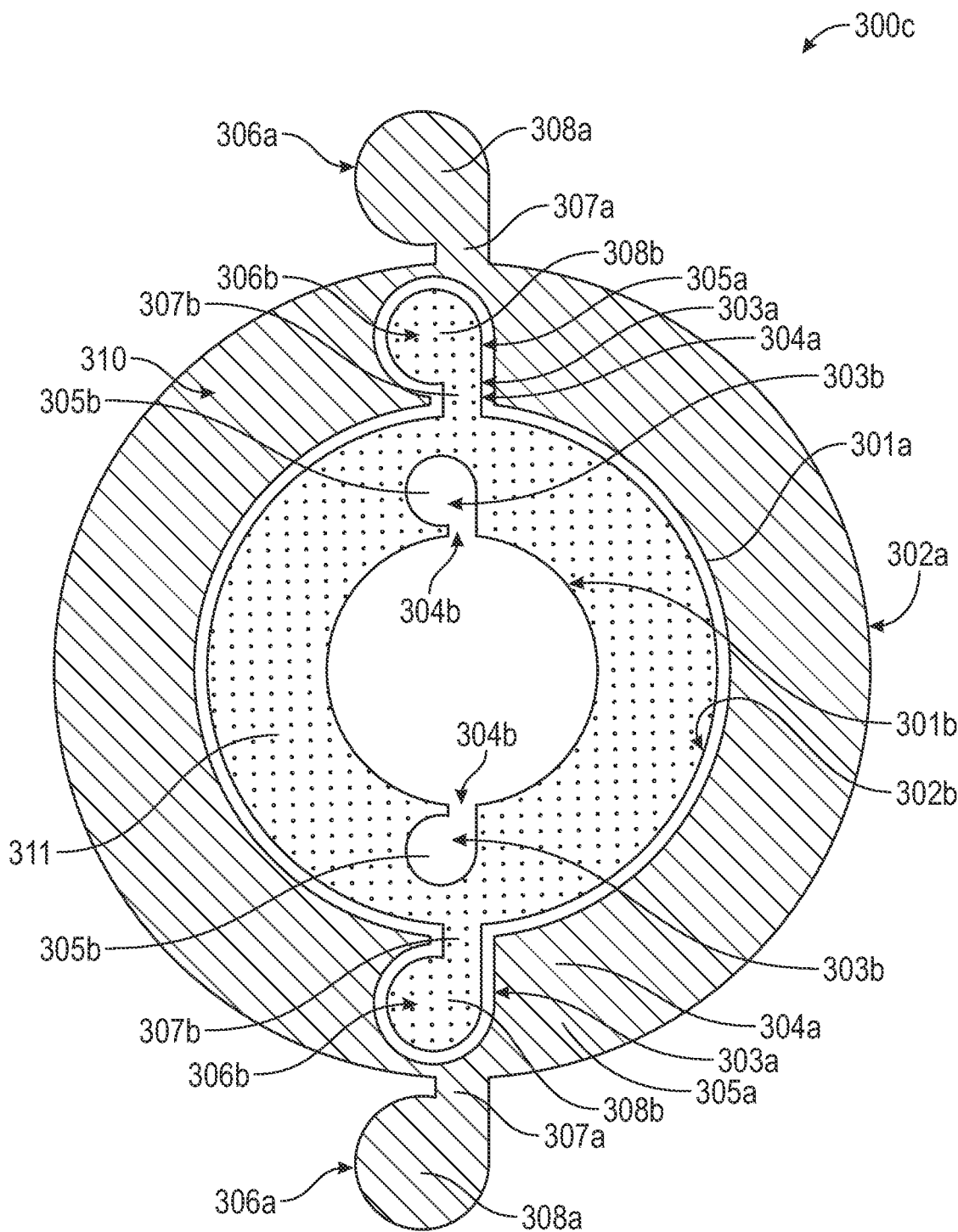
FIG. 3C illustrates ball-in-groove interlocking mechanisms of tubular segments of a telescoping stent.

FIG. 3C illustrates ball-in-groove interlocking mechanisms of two tubular segments that can be used in a telescoping stent, where the two tubular segments are of differing diameters and each tubular segment overlaps along the longitudinal axis with one or more other tubular segments until reaching the final or innermost (smallest diameter) tubular segment, which does not overlap another tubular segment. The ball-in-groove mechanism shown in FIGS. 3A, 3B, 3C, 3D, and 3E is not limited to two tubular segments and can be used in embodiments of the invention that include three or more tubular segments, wherein larger diameter tubular segments overlap and interlock with smaller diameter tubular segments until reaching the final or innermost (smallest diameter) tubular segment, which does not overlap another tubular segment.

Stent 300c comprises a larger diameter tubular segment 310 and a smaller diameter tubular segment 311.

Larger diameter tubular segment 310 is shown as the outermost tubular segment and comprises an interior wall 301a and an exterior wall 302a. Interior wall 301a further comprises one or more receivers 303a. Exterior wall 302a further comprises one or more insertors 306a. Receivers 303a further comprise a proximal end, a distal end, a vestibule 304a, and a track 305a. The vestibule 304a space is narrower than, interior to, and continuous with track 305a, Inserters 306a further comprise a neck 307a and a head 308a. Neck 307a is narrower than, interior to, and continuous with head 308a.

Smaller diameter tubular segment 311 is shown as the interior tubular segment and comprises an interior wall 301b and an exterior wall 302b. Interior wall 301b further comprises one or more receivers 303b. Exterior wall 302b further comprises one or more inserters 306b. Receivers 303b further comprise a proximal end, a distal end, a vestibule 304b, and a track 305b. The vestibule 304b space is narrower than, interior to, and continuous with track 305b. Inserters 306b further comprise a neck 307b and a head 308b. Neck 307b is narrower than, interior to, and continuous with head 308b.

Each receiver 303a of larger diameter tubular segment 310 can house one or more inserters 306b of smaller diameter tubular segment 311. Each neck 307b is disposed in a vestibule 304a. Each head 308b is disposed in a track 305a. Each head 308b can move along the longitudinal axis its track 305a. Each head 308b is larger than the vestibule 304a corresponding to its track 305a so that each insertor 306b cannot exit its corresponding receiver 303a.

Figure 3D:
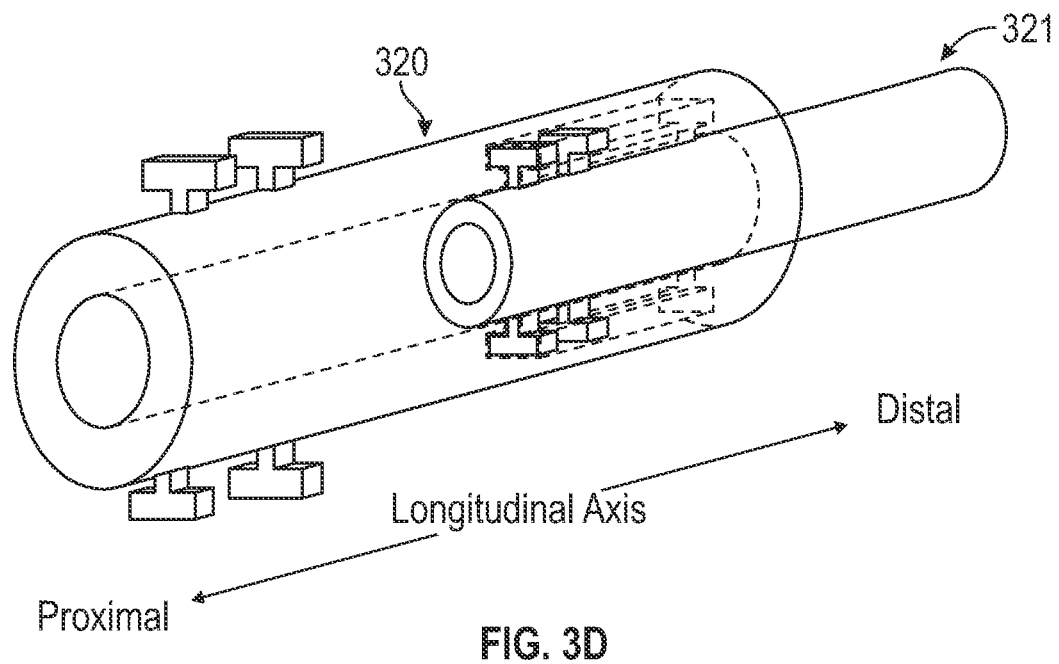
FIG. 3D illustrates overlapping tubular segments of a telescoping stent.
Figure 3E:
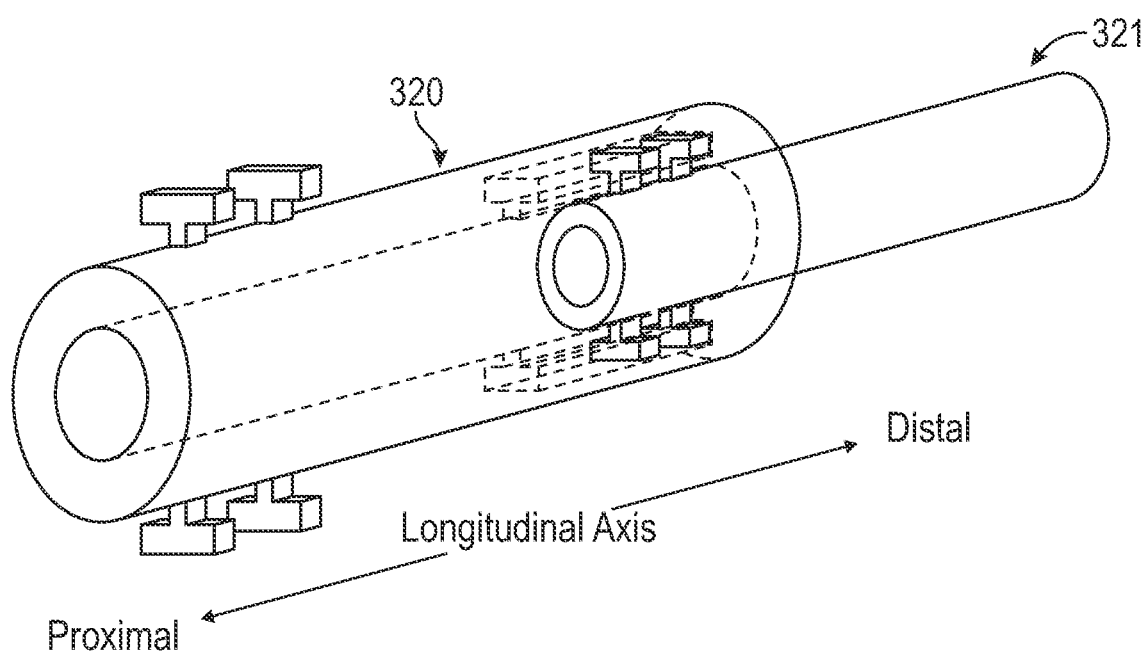
FIG. 3E illustrates overlapping tubular segments of a telescoping stent.

As shown in FIG. 3D, overlapping tubular segments are at maximum overlap when the proximal end of a receiver tracks for outer segment 320 makes contact with the most proximal insertors of inner tubular segment 321 it houses. As shown in FIG. 3E, overlapping tubular segments are at minimum overlap, when the distal end of a receiver track makes contact with the most distal insertor it houses. In certain embodiments, the maximum overlap of tubular segments is 50% or less of the length of the smaller diameter tubular segment.

The ball-in-groove interlocking mechanisms described herein allow for variably telescoping stents that adequately accommodate for expected movement of tubular organs or hollow areas of the body where the stent is deployed. The segments of the device can extend or contract independently and the multiple telescoping segments can float freely within a desired range of motion. The telescoping segments are limited by minimum and maximum overlap as described above.

In certain embodiments, tubular segments comprise medical grade silicone, latex, polyurethane, stainless steel, or plastic. In certain embodiments, receivers comprise medical grade silicone, latex, polyurethane, or plastic. In certain embodiments, insertors comprise medical grade silicone, latex, polyurethane, or plastic.

In one embodiment, a receiver's vestibule can be peripheral to the receiver's track, like that shown in FIG. 3C, or a receiver's vestibule can be central to the receiver's track, like that shown in FIG. 3B. In certain embodiments, a receiver's track can be rounded in shape, like that shown in FIG. 3C, or quadrangular, like that shown FIG. 3B, or any other shape known to one of skill in the art.

In certain embodiments, an insertor's neck can be peripheral to the insertor's head, like that shown FIG. 3C, or an insertor's neck can be central to the insertor's head, like that shown FIG. 3B, An insertor's head can be rounded, like that shown in FIG. 3C, or an insertor's head can be quadrangular, like that shown FIG. 3B, or any other shape known to one of skill in the art. In certain embodiments, insertors' heads are triangular or orthogonal in shape.

In one embodiment, receivers' tracks are round shaped and the insertors' heads are spherical shaped, Thus, receivers' tracks can be viewed as grooves and the insertors' heads can be viewed as balls, allowing for ball-in-groove interlocking mechanisms.

In certain embodiments, tubular segments are about 1.0-5.0 cm in length with a diameter of about 5.0-30.0 mm (15 Fr to 90 Fr), and receivers are about 0.1-4.0 cm in length. In certain embodiments, receivers' tracks are spherical or round in shape and have a diameter of about 2.0-5.0 mm. In certain embodiments, receivers' vestibules are about 1.0-2.0 mm deep (extending into the interior wall) and have an opening diameter of about 1.0-1.9 mm. In certain embodiments, insertors' heads are spherical or round in shape and have a diameter of about 1.9-4.9 mm. In certain embodiments, insertors' necks are about 1.0-2.0 mm in length (extending away from the exterior wall) and have a diameter of about 0.9-1.8 mm.

In alternative embodiments, interior walls do not comprise receivers but further comprise inserters wherein the insertors' heads are inner to the insertors' necks. In certain embodiments, exterior walls do not comprise insertors but further comprise receivers wherein the receivers' tracks are inner to the receivers' vestibules.

In certain embodiments, the innermost tubular segment of the stent, the outermost tubular segment of the stent, or both, can be modified such that the external surface of the stem, the internal surface of the stent, or both, can be smooth. In certain preferred embodiments, the innermost tubular segment of the stoat may comprise an interior wall that does not comprise insertors or receivers. In certain preferred embodiments, the outermost tubular segment of a stent may comprise an exterior wall that does not comprise insertors or receivers.

In further embodiments, the telescoping stent comprises a proximal anchoring member, distal anchoring member, and two or more tubular segments with loop or ball-in-groove interlocking mechanisms. Proximal anchoring member may comprise an inflatable ring. Proximal anchoring member can have a diameter of about 5.0-30.0 mm (15 Fr-90 Fr). in certain embodiments, proximal anchoring member comprises medical staples or sutures. In certain embodiments, a distal anchoring member comprises an inflatable ring. The distal anchoring member can have a diameter of about 5.0-30.0 mm (15 Fr 90 Fr). In certain embodiments, the distal anchoring member comprises medical staples or sutures.

In certain embodiments, the telescoping stent further comprises a one-way sock valve fixed to the distal end of the innermost tubular segment of the telescoping stem. The one-way sock valve may be interlocked with the innermost tubular segment via insertors on the external surface of the valve that interlock with receiver tracks on the internal surface of the innermost tubular segment. The one-way sock valve may also be interlocked to the innermost tubular segment via receiver tracks on the external surface of the valve that interlocks with insertors on the internal surface of the innermost tubular segment. The one-way sock valve can also be fixed to the distal end of a telescoping stent through any other means known in the art. One non-limiting example of a one-way sock valve that can be used with the invention is described in U.S. Pat. No. 10,758,382.

In further embodiments of a telescoping stent with loop interlocking, mechanisms or ball-in-groove mechanisms, the telescoping stent further comprises a sheath, wherein the sheath is affixed to the outside of the proximal and distal segments of the telescoping stent and loosely covers any intermediate segments between them. The sheath may be made of medical grade silicon, latex, polyurethane, plastic, Dacron, or silk. To aid in the delivery of therapeutic agents, the outer surface of the sheath may have an irregular surface created by small bumps and/or raised geometrical figures that can assist in delivering agents while the stent is used. Additionally, in vascular applications, a sheath can be affixed to the interior portion of the proximal and distal segments of the telescoping stunt to permit proper blood flow.

The anchoring mechanisms described herein, especially the use of inflatable rings, allow for variably telescoping stunts that adequately secure to tubular organs or hollow areas of the body where the stent is deployed. The stents may be deployed for extended periods of time without harming or injuring native tissue and without applying too much pressure and/or strain to and/of on the attachment points. The stents can accommodate for movement, as described above, without being displaced, due to dual and non-traumatic securement.

What is claimed is:

1. A telescoping stent, comprising:
  a proximal anchor;
  a distal anchor; and
  two or more tubular segments each comprising a longitudinal axis;
  wherein a first tubular segment of the two or more tubular segments comprises:
    an interior wall comprising a first receiver, the first receiver comprising:
      a first vestibule associated with a first track along the longitudinal axis, wherein the first vestibule is disposed interior to and continuous with the first track, and
    an exterior wall comprising a first insertor having a neck and a head, wherein
      the neck is narrower than and continuous with the head and disposed proximate to the exterior wall relative to the head, said head is disposed in a second vestibule of a second receiver of a second tubular segment, and
      said neck extends through an opening in the second vestibule of the second receiver but said head is too large to exit said opening, and
      said first insertor is movable along the longitudinal axis from a position nearest a proximal end of the second receiver to a position nearest a distal end of the second receiver;
  wherein the first tubular segment has a different diameter relative to the second tubular segment and variably overlaps with said second tubular segment along the longitudinal axis to a maximum overlap and a minimum overlap: and
  wherein the maximum overlap is achieved when the first insertor is in the position nearest the proximal end of the second receiver, and the minimum overlap is achieved when the first insertor is in the position nearest the distal end of the second receiver.

2. The telescoping stent of claim 1, wherein the proximal anchor comprises an inflatable ring, medical staples, and/or sutures.

3. The telescoping stent of claim 1, wherein the proximal anchor has a diameter of about 5.0-30.0 mm (15 Fr-90 Fr).

4. The telescoping stent of claim 1, wherein the distal anchor comprises an inflatable ring, medical staples, and/or sutures.

5. The telescoping stent of claim 1, wherein the distal anchor has a diameter of about 5.0-30.0 mm (15 Fr-90 Fr).

6. The telescoping stent of claim 1, wherein the two or more tubular segments comprise medical grade silicone, latex, polyurethane, stainless steel, or plastic.

7. The telescoping stent of claim 1, wherein the two or more tubular segments are about 1.0-5.0 cm in length with a diameter of about 5.0-30.0 mm (15 Fr-90 Fr).

8. The telescoping stent of claim 1, wherein the first receiver and the second receiver comprise medical grade silicone, latex, polyurethane, or plastic.

9. The telescoping stent of claim 1, wherein the first receiver and the second receiver are about 0.1-4.0 cm in length.

10. The telescoping stent of claim 1, wherein the first vestibule and the second vestibules are spherical, round, triangular, quadrangular, or orthogonal in shape.

11. The telescoping stent of claim 1, wherein the first vestibule and the second vestibules are spherical or round in shape and each have a diameter of about 2.0-5.0 mm.

12. The telescoping stent of claim 1, wherein the first vestibule and the second vestibules are each about 1.0-2.0 mm deep and have a diameter of about 1.0-1.9 mm.

13. The telescoping stent of claim 1, wherein the first insertor comprises medical grade silicone, latex, polyurethane, or plastic.

14. The telescoping stent of claim 1, wherein the heads of the first insertor is spherical, round, triangular, quadrangular, or orthogonal in shape.

15. The telescoping stent of claim 1, wherein the head of the first insertor is spherical or round in shape and has a diameter of about 1.9-4.9 mm.

16. The telescoping stent of claim 1, wherein the neck of the first insertors is about 1.0-2.0 mm deep and has a diameter of about 9-1.8 mm.

17. The telescoping stent of claim 1 further comprising a sheath affixed to the exterior wall of the first tubular segment.

18. The telescoping stent of claim 17 wherein the sheath comprises an irregular outer surface.

19. The telescoping stent of claim 1 further comprising a sheath affixed to the interior wall of the first tubular segment.

20. The telescoping stent of claim 19 further comprising a sheath affixed to an inner wall of the second tubular segment.

21. The telescoping stent of claim 1 further comprising a one-way sock valve.

* * * * *